United States Patent [19]
DeAngelis

[11] Patent Number: 5,713,078
[45] Date of Patent: Feb. 3, 1998

[54] EAR PROTECTION DEVICE FOR SWIMMERS

[76] Inventor: Joanne Marie DeAngelis, 9323 Shore Rd., Apt. 1H, Brooklyn, N.Y. 11209

[21] Appl. No.: 442,792

[22] Filed: May 18, 1995

[51] Int. Cl.[6] .............................. A63B 33/00; A42B 3/16
[52] U.S. Cl. .......................... 2/209; 2/428; 2/909
[58] Field of Search .................. 2/209, 423, 428, 2/430, 2.14, 918, 68, 909

[56] References Cited

U.S. PATENT DOCUMENTS

| | | | |
|---|---|---|---|
| 2,593,892 | 4/1952 | Kindel | 2/68 X |
| 2,738,514 | 3/1956 | Gondell | 2/209 |
| 4,279,039 | 7/1981 | Drew | 2/68 X |
| 4,612,672 | 9/1986 | Schrack | 2/918 X |
| 4,670,911 | 6/1987 | Dunford | 2/209 |
| 4,802,245 | 2/1989 | Miano | 2/918 X |
| 4,805,239 | 2/1989 | Ciago | 2/209 X |
| 5,421,037 | 6/1995 | Schulze | 2/209 X |
| 5,617,589 | 4/1997 | Lacore et al. | 2/209 X |

FOREIGN PATENT DOCUMENTS 0105365  9/1942  Sweden ..................... 2/209

OTHER PUBLICATIONS

Gershman, "Self Adhering Nylon Tapes", J.A.M.A., vol. 68. No. 7, Oct. 1958.

*Primary Examiner*—Peter Nerbun
*Attorney, Agent, or Firm*—Christa Hildebrand

[57] ABSTRACT

This invention provides an ear protector to prevent water from entering the ear during watersport activities like swimming, surface snorkeling or child's play in the water. It provides for waterproof ear pieces which are adhered to a head band worn either over the head and under the chin or, in combination with a viewing piece, around the front of the head to the rear of the head. While the ear pieces and viewing piece are watertight around the ears or eyes due to suction of suitable material, the band can also be tightened to further promote tightness against water.

1 Claim, 4 Drawing Sheets

EAR PROTECTION DEVICE FOR SWIMMERS

BACKGROUND OF THE INVENTION

This invention relates to an ear protection device for swimmers, and more particular, to ear covers useful to prevent foreign objects to enter the ear and cause irritation or ear infection.

1. Field of the Invention

Several ear protection devices are available for various activities, including sports activities. However, for water sports, in particular for swimmers or under-water activities, the only protection readily available are different forms of ear plugs. Certain people with sensitive ear channels do not tolerate plugs in their ear openings, even if the plugs are made of soft material which conforms to the form and size of the ear channel. In particular, children are likely not to tolerate ear plugs of any sort, although they have great need to protect their ears. Many children are introduced to the joys of watersport at an early stage of their lives and they are humans most prone to suffer from either ear infections from bacteria entering their ears, or simply water logged ears which is annoying to them. Often, people enjoying water sports, wear gargles or masks to protect their eyes from chlorinated water or ocean water, but in order to protect their ears they have to resort to plugs which have the disadvantages discussed above. Thus, it is the object of this invention to present an ear protection device which does not have the disadvantages as the known ear plugs have.

2. Description of the Related Art

Ear protecting gear for many activities is known. Many times, the gear is in combination with protecting other parts of the head, either the head in general or eyes in particular. Due to growing competitiveness of all sports, there is more emphasis on protecting the head and also ears from impact, see for example U.S. Pat. No. 5,184,354. Another line of ear protection is developed to protect the ear from excessive noise, see for example U.S. Pat. No. 4,856,089 where a combined eye and ear gear was disclosed to protect the wearer during hand gun target practice. Similar reason for providing a combined eye/ear protection was provided in U.S. Pat. No. 3,943,925, where ear plug are disclosed in combination with eye glasses. However, it is apparent that none of these disclosures are suitable for adaption for ear protection from water entering the ear and thereby protecting the ear from infection or discomfort.

SUMMARY OF THE INVENTION

It is therefore an object of the present invention to provide an ear protection device for various water activities, including swimming or surface snorkeling. In particular, the ear protection device should be comfortable enough to suit children and even babies who are particularly sensitive to water entering their ear which causes them discomfort coupled with dislike of water. The present invention provides a solution: It protects the ears from water entering and may also at the same time, protect the eyes when from water entering.

According to the present invention, an ear protection is provided by closing ears off from water entering ears utilizing a head portion, two ear shells formed to fit over each ear, a chin strap to facilitate closing and serving to control the tightness around the head. The ear shells are made of soft, waterproof rubberized material, such as a closed-pored foam material. The ear shells are disposed on the band which forms a head portion and a chin strap, preferably made of omni-directional stretch material, such as disclosed in U.S. Pat. No. 4,761,324. The band of the present invention extend over the head and forms a chin strap. The chin strap may be made of two bands with closing mechanism attached to the band, such as two pieces of Velcro® that is a strip of hook and loop fasteners, or one strip may provide a buckle accepting the other strip for tightening. Several closing means are known in the art.

In one preferred embodiment, the head portion and chin strap are formed in one unit with the ear shells attached on the unit. The band may be material such as poly vinyl or neoprene rubber, but any elastic material would be feasible. The ear shells are preferably made of a non-water absorbent material and adhered to the band. It is even contemplated to have different sizes of ear protectors to fit adults as well as different aged children.

One other preferred embodiment provides for ear protection which is not worn over the top of the head but more like goggles or diving masks. This unit has a band which extends to the back of the head, a viewing portion in front of the eyes, two soft, waterproof rubberized ear shells formed to fit over each ear and adhered to the band, a closing means located at the back of the head. The band that extends to the back of the head can also be split into an upper portion and a lower portion in order to suit different fits and accommodate for different hear styles, i.e. pony tails etc. It is within the invention to form the viewing portion in front of the eyes like two goggles connected by a bridge. Or it is contemplated to provide a viewing piece similar to a diver's mask, that has one piece for viewing which fits over both eyes. It is only important to provide the viewing piece as part of the ear protecting unit in as the viewing piece (or pieces) fits on the face in a watertight fashion and at the same time are in combination with the ear pieces which fit watertight around the ears.

While the ear protection of this invention is mainly concerned with protection from water, it is not limited to use the ear protector only in connection with water but also provides protection from wind.

DETAILED DESCRIPTION OF THE PREFERRED EMBODIMENTS

Figure 1:
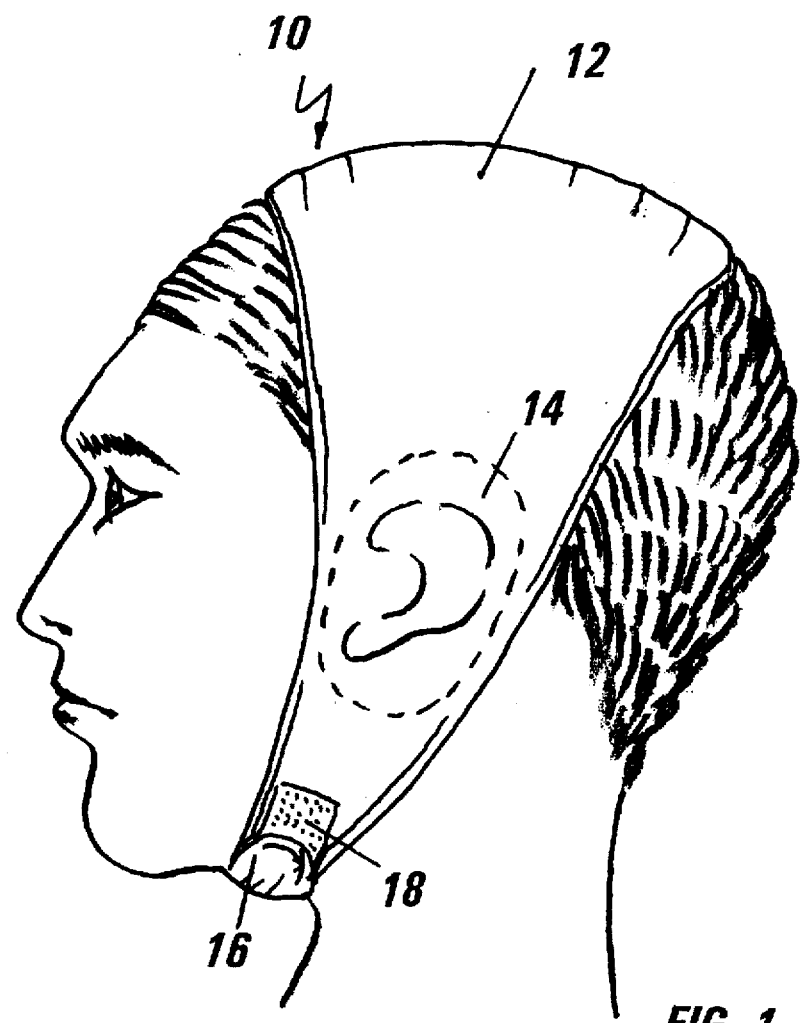
FIG. 1 shows as ear protection device for ears suitable to be worn over the head and tightened under the chin.
Figure 1A:
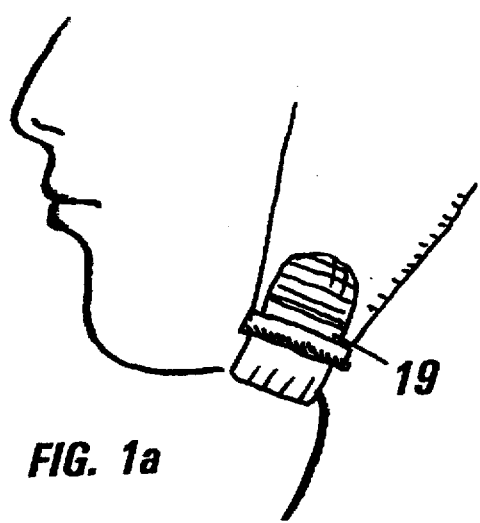
FIG. 1a shows another closing means for the device shown in FIG. 1.

Turning now to the figures, FIG. 1 illustrates one embodiment of the invention. The ear protection device 10 is worn across the head. Provided is a band 10 having a head portion 12, ear shells 14 on the inside, either integral or adhered to the band, and a chin strap 16 shown being closed by a Velcro® strip 18. However, a non-corrosive buckle 19 shown in FIG 1a is also within this invention.

Figure 2:
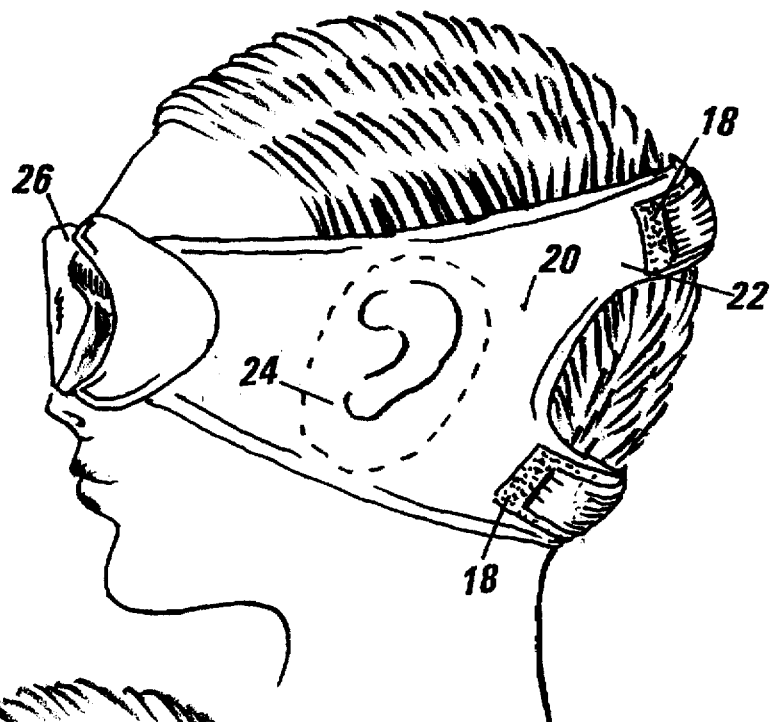
FIG. 2 shows a protection for ears with integrated viewing portions.
Figure 2A:
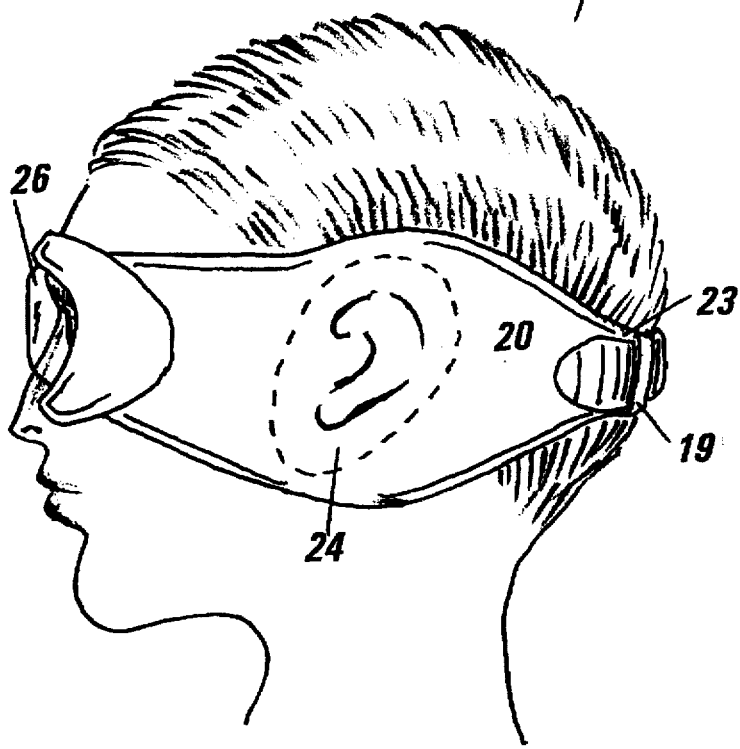
FIG. 2a shows a another closing means for the device shown in FIG. 2.

FIG. 2 illustrates an embodiment which combines the ear protective device with goggles. Provided here is a band 20 worn across the back of the head and the eyes. The band 20 has a rear head portion 22, or 23 in FIG. 2a, ear shells 24 on the inside, either integral or adhered to the band, and integrated goggle 26. The goggles adhere to the face as any known goggles with two eye cups do, but they depart from the traditional design in as they are integrated into the band. A silicon-type material is bonded or sealingly affixed to the band material. The band in the rear of the head may be a divided strip 22 or a single 23, as shown in FIG. 2. The band may be closed as well as comfortably tightened by one or two Velcro® strips 18. However, a noncorrosive buckle 19 shown in FIG. 2a is also within this invention.

Figure 3:
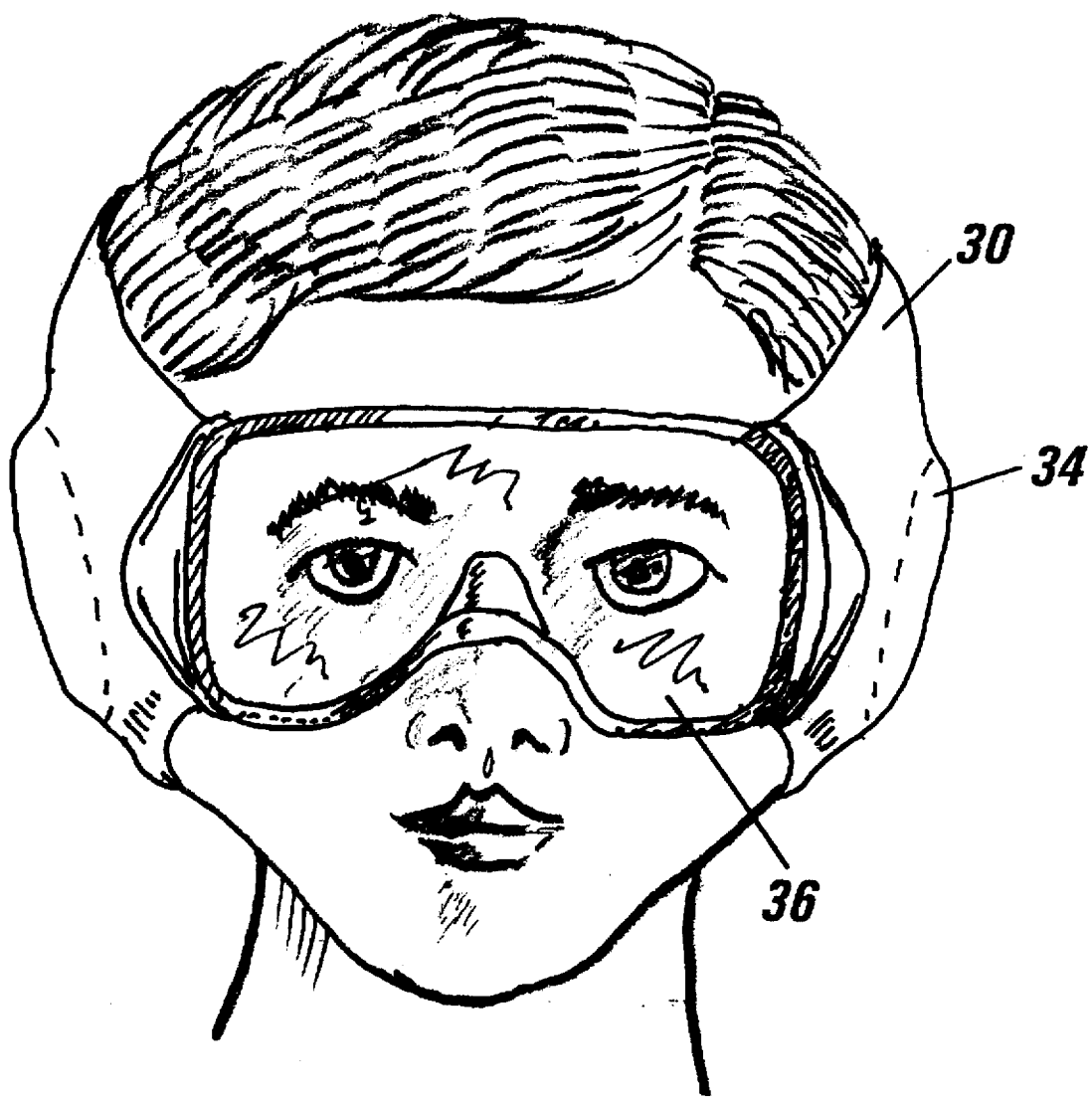
FIG. 3 shows a protection for ears with a different viewing portion.
Figure 4:
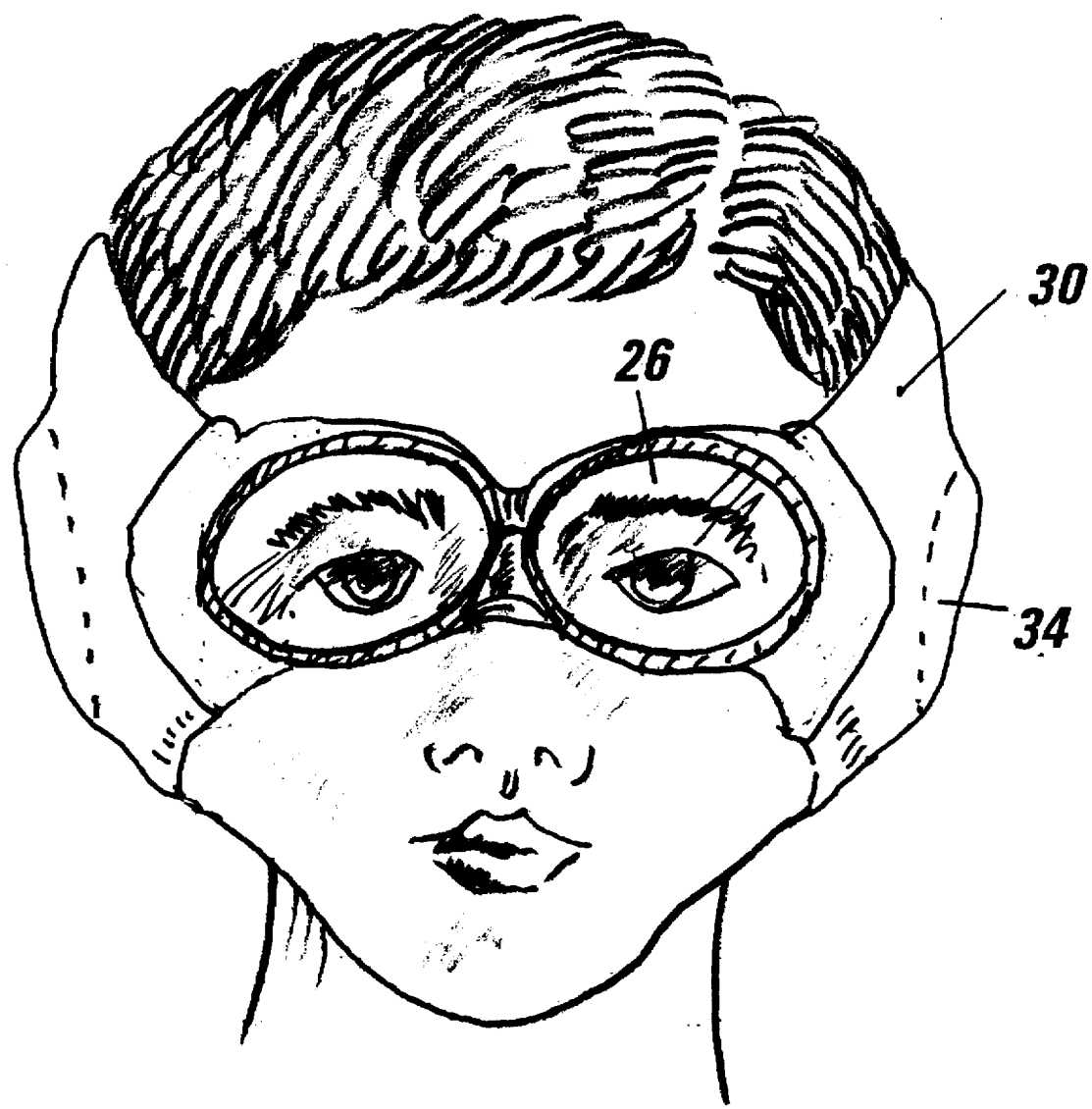
FIG. 4 shows a protection for ears with a viewing portion having two eye cups.

FIG. 3 illustrates another embodiment which combines the ear protective device with diving mask viewing device FIG. 4 illustrates another embodiment which combine the ear protection device with two eye cups. Provided here is a band 30 worn across the back of the head and the eyes. The band 30 has a rear head portion, similar to the embodiment of FIG. 2, ear shells 34 on the inside, either integral or adhered to the band, and integrated diving mask 36. The mask adheres to the face as any known mask does. However, the design of this mask departs from the traditional mask design in as the mask of the invention is integrated into the band. A silicon-type material is bonded or sealingly affixed to the band material. The band in the rear of the head may be the same divided strip 22 or a single 23, as shown in FIG. 2. The band may be closed as well as comfortably tightened by one or two Velcro® strips 18. However, a non-corrosive buckle 19 shown in FIG. 2a is also within this invention.

What is claim is:

1. Ear protection device for closing ears off from water entering ears, comprising:

a band;

a viewing portion;

two ear shells formed to fit over each ear and fixedly disposed within the band;

a closing means comprising two closing strips;

wherein the ear shells are made of soft, waterproof, rubberized material, the viewing portion comprises a water-tight seal for sealing off water to enter eyes, wherein the band is made of omni-directional stretch material and wherein the closing strips comprise hook and loop fasteners and wherein the band, the viewing portion, the ears shells and closing means are connected such as to form one permanently fixedly connected integral unit.

* * * * *